United States Patent [19]

Voydeville

[11] Patent Number: 5,609,634
[45] Date of Patent: Mar. 11, 1997

[54] INTERVERTEBRAL PROSTHESIS MAKING POSSIBLE ROTATORY STABILIZATION AND FLEXION/EXTENSION STABILIZATION

[76] Inventor: Gilles Voydeville, 90 quai Claude le Lorrain, Nancy, France, 54000

[21] Appl. No.: 362,583

[22] PCT Filed: Jun. 30, 1993

[86] PCT No.: PCT/FR93/00664

§ 371 Date: Feb. 8, 1995

§ 102(e) Date: Feb. 8, 1995

[87] PCT Pub. No.: WO94/01057

PCT Pub. Date: Jan. 20, 1994

[30] Foreign Application Priority Data

Jul. 7, 1992 [FR] France .................................. 92 08391

[51] Int. Cl.$^6$ .............................. A61F 2/44; A61B 17/56
[52] U.S. Cl. ................................................ 623/17; 606/61
[58] Field of Search ..................... 606/61, 60; 623/13, 623/17, 18

[56] References Cited

U.S. PATENT DOCUMENTS

| | | | |
|---|---|---|---|
| 4,643,178 | 2/1987 | Nastari et al. . | |
| 4,728,329 | 3/1988 | Mansat | 623/13 |
| 4,795,466 | 1/1989 | Stuhmer et al. | 623/13 |
| 4,917,700 | 4/1990 | Aikins . | |
| 5,011,484 | 4/1991 | Breard | 606/61 |

FOREIGN PATENT DOCUMENTS

| | | |
|---|---|---|
| 0249346 | 12/1987 | European Pat. Off. . |
| 0277280 | 8/1988 | European Pat. Off. . |
| 0322334 | 6/1989 | European Pat. Off. . |
| 0392124 | 10/1990 | European Pat. Off. . |
| 2662600 | 12/1991 | France . |

*Primary Examiner*—David Isabella
*Attorney, Agent, or Firm*—Young & Thompson

[57] ABSTRACT

A prosthesis including (a) a flexible ligament (1) with a first narrowed thinner portion (2) and a second wider portion (3) forming an extension of, and having a greater width and thickness (e2) than, the first portion, which portion may be passed around the spinous processes (12) of two adjacent vertebrae (L5, L4) in a figure eight pattern, whereas the second portion circles around the processes; (b) a semi-flexible interprocess block (6) with two pairs of through-channels (7, 8) having differing cross-sections and receiving the respective portions of the ligament; and (c) members (4, 5) for joining the ends of the ligament. The prosthesis prevents sagittal and frontal lumbar vertebral rotational instability.

3 Claims, 4 Drawing Sheets

INTERVERTEBRAL PROSTHESIS MAKING POSSIBLE ROTATORY STABILIZATION AND FLEXION/EXTENSION STABILIZATION

FIELD OF THE INVENTION

The present invention relates to an intervertebral prosthesis.

BACKGROUND OF THE INVENTION

Various types of intervertebral retention prostheses have previously been made, either rigid or flexible, the function of which is to eliminate lumbar vertebral frontal and sagittal rotatory instability. The rigid prostheses comprise plates, rods with hooks, and the flexible prostheses are formed by ligaments associated with rigid or flexible blocks.

However, these known ligamentary systems do not make it possible to stabilize flexion/extension and rotation in a satisfactory manner.

OBJECT OF THE INVENTION

The aim of the invention is therefore to produce an intervertebral prosthesis of the ligamentary type, arranged so as to be capable of stabilizing flexion/extension and rotation in an entirely satisfactory manner.

SUMMARY OF THE INVENTION

According to the invention, the intervertebral prosthesis comprises:

a) a flexible ligament comprising a first, thin part of small width and of small thickness, and a second, wide part in continuation of the first, of greater width and thickness than the first part, the first part being intended to make possible lacing in a figure of eight around the spinous processes of two adjacent vertebrae, while the second part is adapted to carry out a perispinous encircling, b) a semi-flexible interspinous block, in which two pairs of continuous ducts of different section are cut, which are adapted for passage of the two respective parts of the ligament, c) means for closing the ligament on itself.

According to an advantageous embodiment of the invention, the two ducts for passage of the thin part are juxtaposed in the central part of the block and intercommunicate via a central opening which makes it possible to cross two strands of the thin part of the ligament.

The prosthesis according to the invention therefore makes it possible to carry out simultaneously stabilization of the vertebrae in flexion/extension by virtue of the perispinous encircling of the wide part of the ligament and stabilization in rotation by virtue of oblique passage between the spinous processes of the thin part of the ligament.

The latter can be made of an appropriate material, for example polyester or the material known under the trade mark "DACRON" (polyethylene terephthalate), made of a braiding in different directions.

BRIEF DESCRIPTION OF THE DRAWINGS

Other features and advantages of the invention will appear in the course of the description which follows and is given with reference to the attached drawing which illustrates en embodiment thereof by way of non-limiting example.

DETAILED DESCRIPTION OF THE INVENTION

Figure 1:
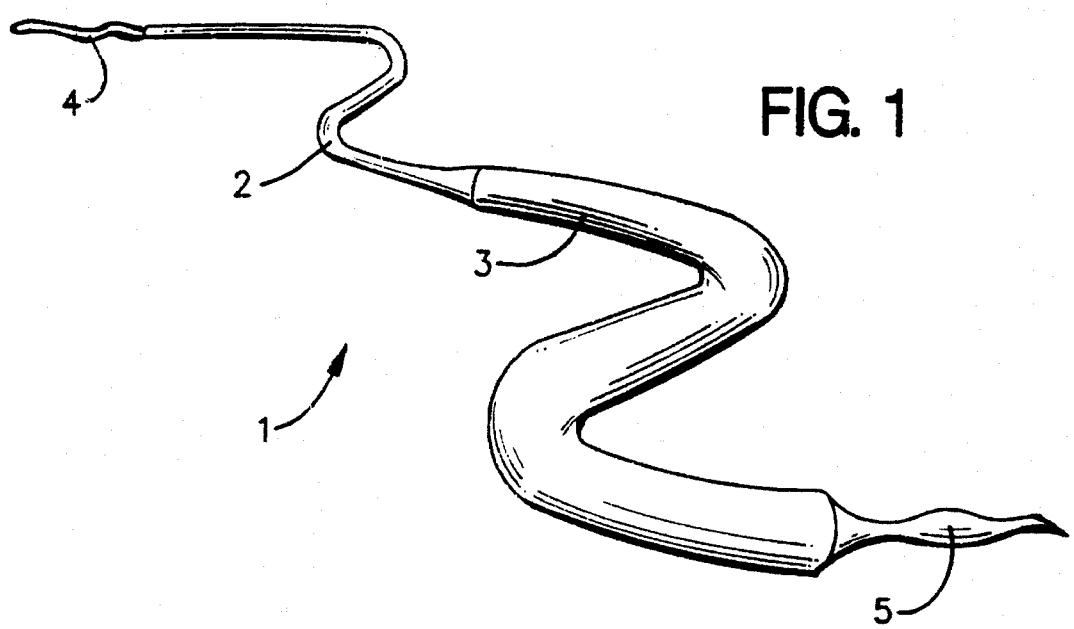
FIG. 1 is a view in perspective of an embodiment of the ligament of the intervertebral prosthesis according to the invention.
Figure 2:
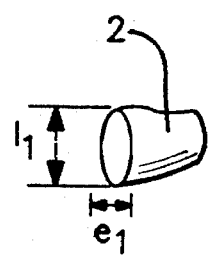
FIGS. 2 and 3 are views in partial perspective of lengths of the thin and wide parts respectively of the ligament in FIG. 1, showing the difference in section.

The prosthesis to which the invention relates comprises a flexible ligament 1 consisting of two parts: a first, thin part 2, of small width and of small thickness, and a second, wide part 3, in continuation of the first part 2, of greater width and thickness than the part 2. By way of non-limiting indicative numerical example, the width 11 (FIG. 2) of the thin part 1 may be 4 mm and its thickness e1 1 mm, while the width 12 of the wide part 3 may be 8 mm, its thickness e2 being 2 mm.

The ends of the two parts 2, 3 are extended by threads 4, 5 intended to make possible passage of the ligament 1. The ligament is sewn on itself via four or five points in an X shape.

Figure 4:
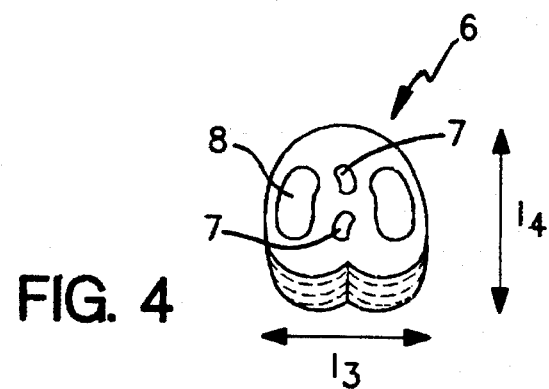
FIG. 4 is a view in perspective of an embodiment of the block of the prosthesis according to the invention.
Figure 3:
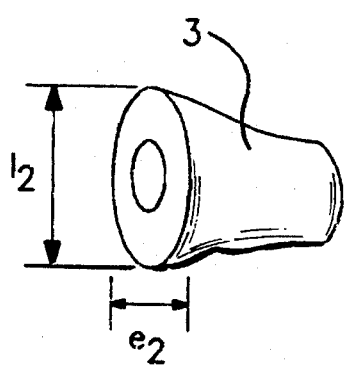
Figure 5:
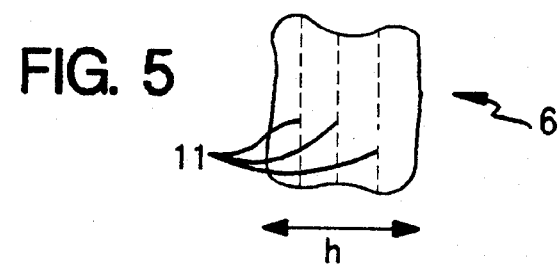
FIG. 5 is a view from above of the block in FIG. 4.
Figure 6:
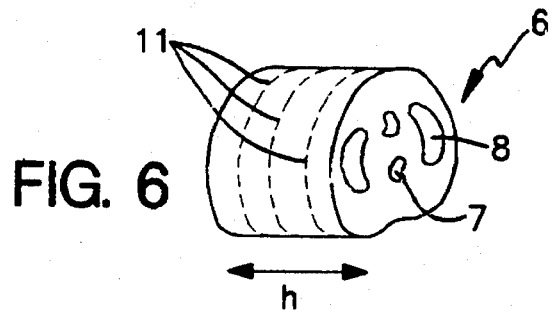
FIG. 6 is a view in perspective of the block at a different angle to that in FIG. 4.
Figure 9:
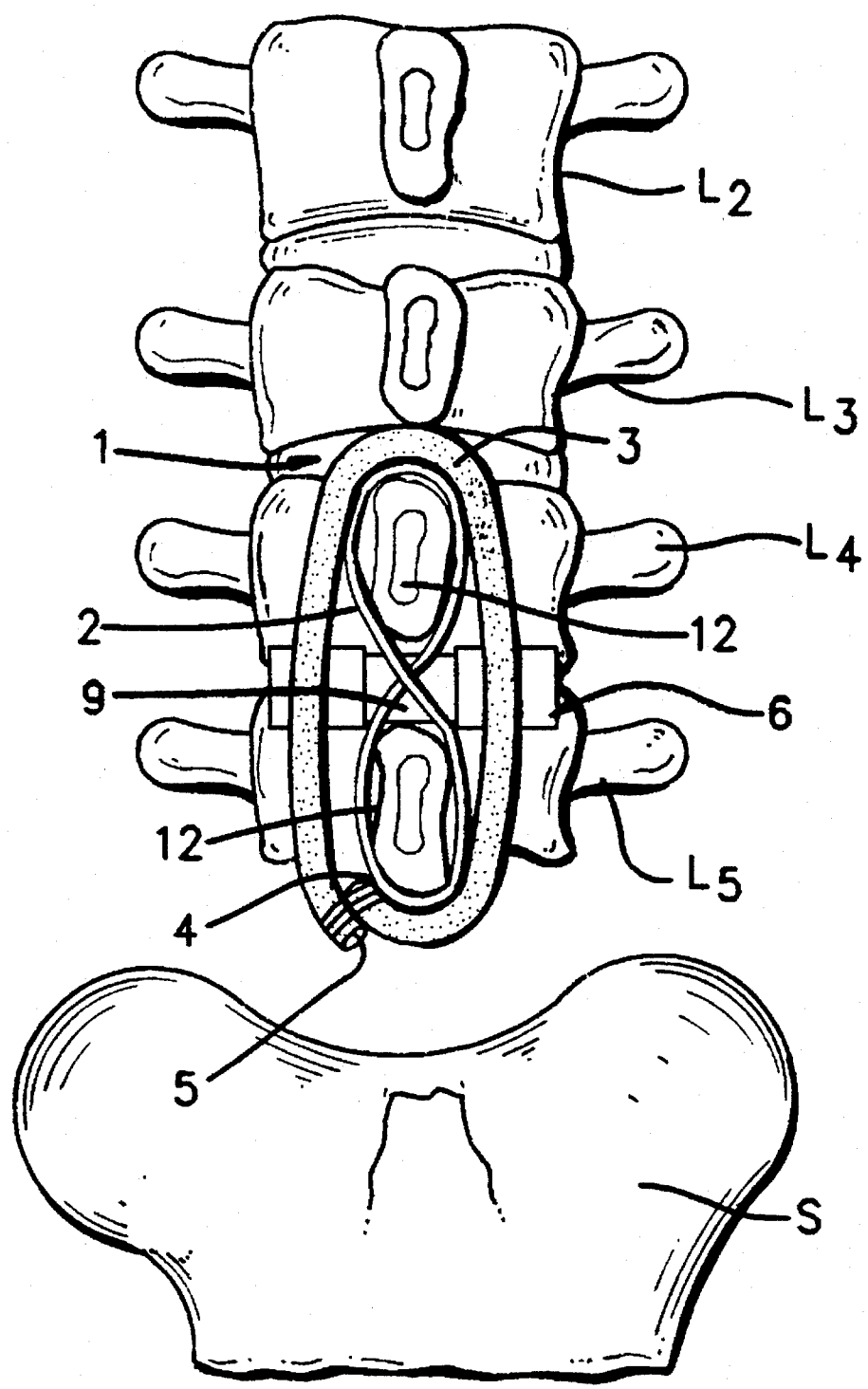
FIG. 9 is a view in rear elevation of the lumbar vertebrae provided with the intervertebral prosthesis in FIG. 8.

The prosthesis also comprises an interspinous block 6 (visible in particular in FIGS. 4 to 6) which is semi-flexible and in which two pairs of continuous ducts of different sections are cut: a first pair of ducts 7 juxtaposed in the central part of the block and of small section corresponding to the section of the narrow part 2 of the ligament 1, and two ducts 8 each placed on one side of the two ducts 7 and of very much greater section than that of the ducts 7 and intended to receive the wide part 3 of the ligament 1. The two central ducts 7 intercommunicate via a central opening 9 made in the separation partition of the two ducts 7 (FIG. 9). The ducts 7 and 8 are approximately parallel with one another and pierce the block 6 right through. The block 6 may have different heights so as to set the vertebrae in slight distraction.

This block is made of the same material as the ligament 1 and rendered semi-flexible by means of, for example, reinforcement stitching lines 11 which make it possible to increase its rigidity under compression.

Fitting the intervertebral prosthesis consisting of the ligament 1 and of a block 6 is carried out in the following manner.

Figure 7:
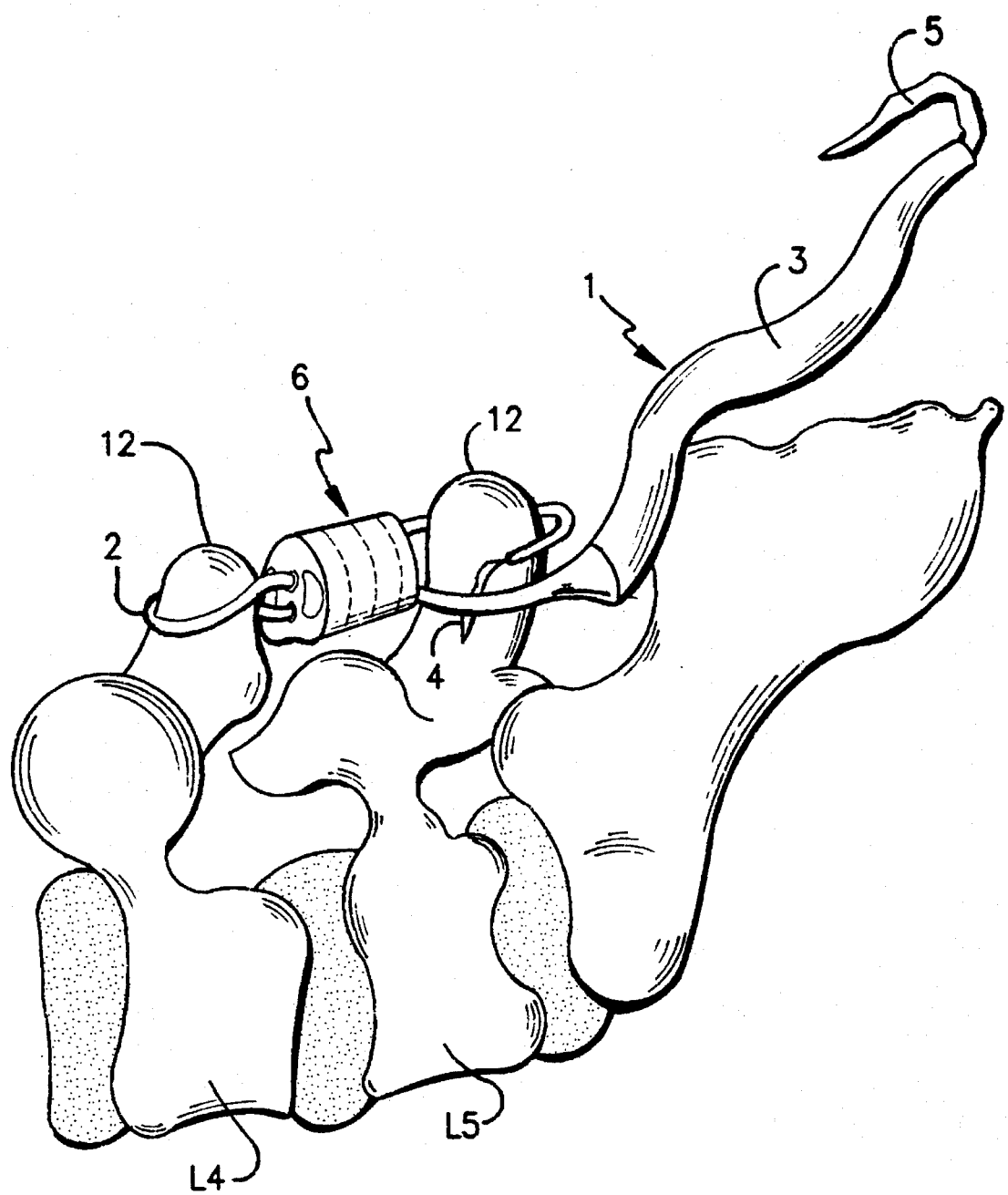
FIG. 7 is a view in perspective of the intervertebral prosthesis in FIGS. 1 to 6 in the course of mounting on the spinous processes of two adjacent lumbar vertebrae.
Figure 8:
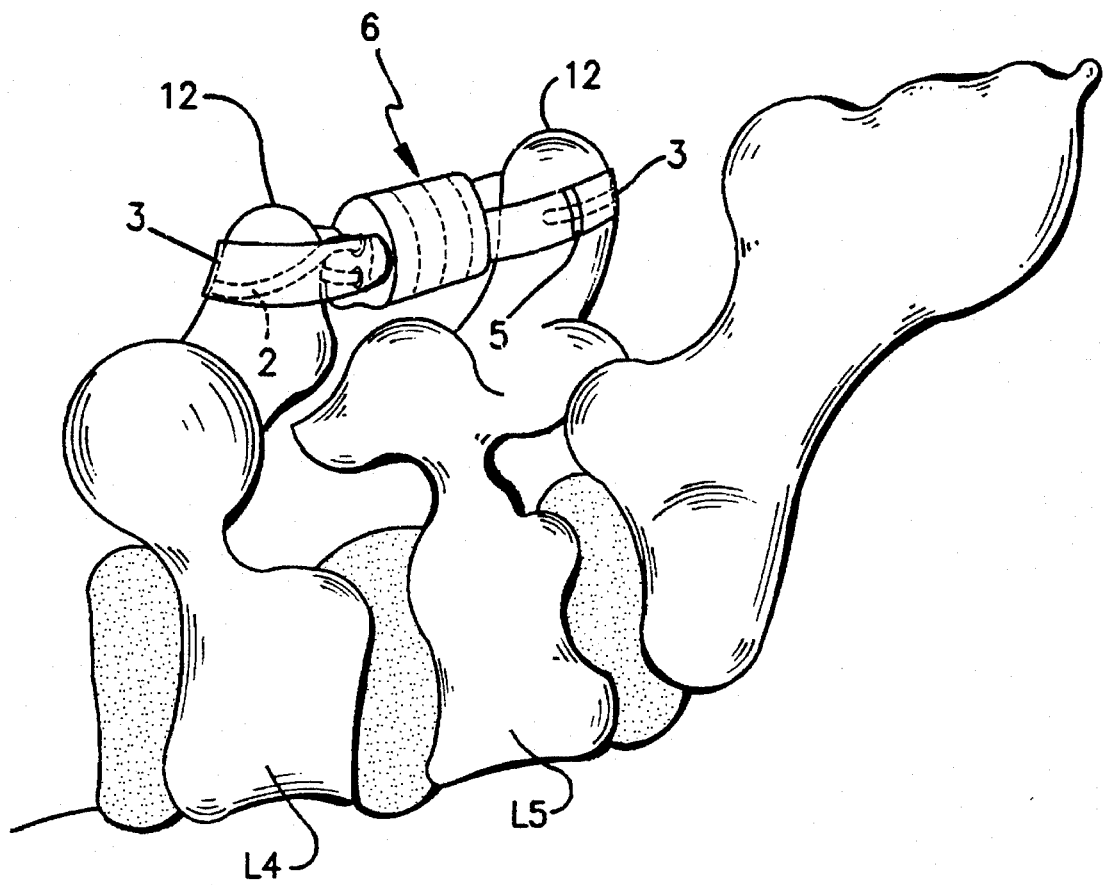
FIG. 8 is a view in perspective similar to FIG. 7, showing the mounting of the prosthesis when completed.

In FIGS. 7 to 9, the final four lumbar vertebrae L5, L4, L3, L2 and the sacrum S can be seen, the prosthesis being intended to be fitted on the first two lumbar vertebrae L5, L4. The surgeon first of all arranges the block 6 between the spinous processes 12 so that the ducts 7 extend on either side of the central plane of the spinous processes. The surgeon then carries out lacing in a figure of eight around the spinous processes 12 by means of the thin part 2 of the ligament 1, making this thin part pass successively into one of the ducts 7 and then into the central orifice 9 and from there into the second duct 7. The surgeon then carries out a first encircling of the spinous process 12 of the vertebra L4 and reintroduces the end of the thin part 2 into one of the ducts 7, the orifice 9 and the second duct 7, finishing the lacing with a final loop around the spinous process 12 of the vertebra L5. At this stage, a suture is made between the two strands of the thin part 2 by means of the thread 4.

The surgeon then carries out an interspinous encircling by means of the wide part 3 around the two spinous processes 12, making the wide part 3 pass through the lateral ducts 8. Once complete looping of the spinous processes 12 has been carried out, the surgeon finishes the fitting by carrying out a suture of the two ends of the wide part 3 one on the other by means of the thread 5.

By way of non-limiting numerical examples, completing the indications given above relative to the section of the narrow 2 and wide 3 parts of the ligament 1, the latter can be of two types: one for short mounting, one for long mounting. For short mounting, the ligament 1 measures, for example, 40 cm divided into 20 cm for the thin part 2 and 20 cm for the wide part 3. For long mounting, the ligament 1 measures 60 cm, 30 cm for the thin narrow part 2, 30 cm for the wide part 3. The corresponding blocks 6 have a width 13 of 15 mm (FIGS. 4 to 6) and a length 14 of 15 mm, while their height h may vary between 8 and 22 mm.

The resistance of the ligament 1 to traction is advantageously greater than 300 kg and its stiffness is greater than 500 N/mm.

The ligament 1 and the block 6 are advantageously provided with a radio-opaque filament.

The intervertebral prosthesis according to the invention makes it possible, by virtue of its shape and the restricted volume which it occupies, to fix the vertebrae L5, L4 both in rotation and in flexion/extension. In fact, previously used ligaments do not make it possible to carry out lacing in a figure eight around the vertebrae and then to make this ligament pass around these again.

The lacing is carried out in all directions with the ligament 1 according to the invention, which each time passes through the interspinous block 6, rigidifying the mounting.

The block 6 can be considered semi-elastic because it is sufficiently flexible not to bring about any direct conflict with the bone and sufficiently rigid to maintain a certain distraction between the spinous processes.

As a variant, it is possible in particular to replace the suture threads 4, 5 by any other appropriate means, such as a metal staple or a rivet.

The indications for fitting the ligament 1 and the block 6 of the prosthesis to which the invention relates are in particular lumbar instabilities. Lumbar instability is an ailment relative to all types of pathological rachides, in particular narrow lumbar ducts, isthmian lyses and slipped discs.

I claim:

1. An intervertebral prosthesis which comprises:

a semi-flexible interspinous block configured to be disposed between adjacent spinous processes, said block having two pairs of continuous ducts of different cross-sections formed therethrough, a flexible ligament having a first thin part of small width and thickness, and a second wide part in continuation of said first part, of greater width and thickness than said first part, wherein said ducts are adapted for passage of each of said first and second parts, respectively, of the ligament such that said first part is adapted to be laced through one of said pair of ducts in a figure eight around the spinous processes of two adjacent vertebrae; and the second part of the ligament is adapted to be laced through the other of said pair of ducts for perispinous encircling, and means for closing the ligament on itself.

2. An intervertebral prothesis as claimed in claim 1, wherein said means for closing the ligament are threads which comprise ends of said two parts.

3. An intervertebral prothesis as claimed in claim 1, wherein the two ducts for passage of the thin part are juxtaposed in a central part of the block and intercommunicate through a central opening which makes it possible to cross two strands of the thin part of the ligament, and the two ducts for passage of the wide part are arranged on each side of the ducts for passage of the thin part.

* * * * *